(12) United States Patent
Thielemans

(10) Patent No.: US 7,756,307 B2
(45) Date of Patent: Jul. 13, 2010

(54) METHOD OF, AND SOFTWARE FOR, CONDUCTING MOTION CORRECTION FOR A TOMOGRAPHIC SCANNER

(75) Inventor: Kris Filip Johan Jules Thielemans, London (GB)

(73) Assignee: Hammersmith Imanet Limited, London (GB)

( * ) Notice: Subject to any disclaimer, the term of this patent is extended or adjusted under 35 U.S.C. 154(b) by 542 days.

(21) Appl. No.: 10/576,004

(22) PCT Filed: Oct. 14, 2004

(86) PCT No.: PCT/GB2004/004379

§ 371 (c)(1),
(2), (4) Date: Apr. 17, 2006

(87) PCT Pub. No.: WO2005/038491

PCT Pub. Date: Apr. 28, 2005

(65) Prior Publication Data

US 2007/0147589 A1    Jun. 28, 2007

(30) Foreign Application Priority Data

Oct. 17, 2003    (GB) ................. 0324374.8

(51) Int. Cl.
*G06K 9/00* (2006.01)
*G01N 23/06* (2006.01)

(52) U.S. Cl. ............... 382/128; 382/131; 382/154; 378/207; 378/4; 378/21; 250/363.08

(58) Field of Classification Search ........ 378/807, 378/4, 21, 131, 19, 51, 146; 250/363.08, 250/374, 385.1, 385.2, 375, 386, 387; 382/131
See application file for complete search history.

(56) References Cited

U.S. PATENT DOCUMENTS 4,639,941 A * 1/1987 Hounsfield ............ 378/11

(Continued)

FOREIGN PATENT DOCUMENTS

GB    2250164    5/1992

OTHER PUBLICATIONS

An Accurate Method for Correction of Head Movement in PET; Paul Bühler, Uwe Just, Edmund Will, Jörg Kotzerke, and Jörg van den Hoff; Aug. 2004.*

(Continued)

*Primary Examiner*—Wesley Tucker
*Assistant Examiner*—Nancy Bitar
(74) *Attorney, Agent, or Firm*—Robert F. Chisholm

(57) ABSTRACT

A method of conducting motion correction for a tomographic scanner including a detector array for detecting radiation to generate detector data. The method comprises storing detector data collected during a data acquisition period, the detector data being indicative of directions along which radiation is detected and quantities of radiation detected in different of said directions. The method involves storing movement data representing movement of the subject during the data acquisition period and motion correcting the detector data using the movement data and a motion correction algorithm to calculate motion corrected detector data. The motion correcting step comprises realigning directions of at least some of said detector data on the basis of said movement data and altering quantities of at least some of said detector data on the basis of said movement data, such that at least some of said detector data are both realigned and altered in quantity due to movement of the subject, some detector data are very small and subject to large noise levels. In these cases, the detector data quantities are altered using calculation of estimates from other, more reliable, detector data.

13 Claims, 6 Drawing Sheets

U.S. PATENT DOCUMENTS

| | | | |
|---|---|---|---|
| 6,490,476 | B1* | 12/2002 | Townsend et al. ............ 600/427 |
| 6,631,284 | B2* | 10/2003 | Nutt et al. ................... 600/427 |
| 6,980,683 | B2* | 12/2005 | Jones ......................... 382/131 |
| 2008/0224050 | A1* | 9/2008 | Thielemans et al. ......... 250/362 |

OTHER PUBLICATIONS

The design and implementation of a motion correction scheme for neurological PET., Bloomfield et al , 2003.*

Model-Based Scatter Correction for Fully 3D PET, Ollinger et al, IEEE 1994.*

Image Reconstruction of Motion Corrected Sinograms ; IEEE 2004, Thielmans et al.*

Use of forward projection to correct patient motion during SPECT imaging, LEe KJ, 1998, pp. 171-187.*

Bloomfield P.et al The design and implementation of a motion correction scheme for neurological PET, Apr. 2003, pp. 959-978.*

Lee K.J. and Barber D.C.: "Use of forward projection to correct patient motion during SPECT imaging" Phys. Med. Biol., vol. 43,. 1998, pp. 171-187.*

Qi J. and Huesman R.H.: "Correction of Motion in PET Using Event-Based Rebinning Method: Pitfall and Solution" J. Nucl. Med., Jun. 19, 2002, p. 146P.*

Bloomfield P, et.al. "The Design and Implementation of a Motion Correction Scheme for Neurological PET", Phys. Med. Biol., vol. 48, Apr. 2003, pp. 959-978.

Fulton R.R., et.al., "Correction for Head Movements in Positron Emission Tomography Using an Optical Motion Tracking System", Nuclear Science Symposium Conference Records, 2000 IEE Lyon, France Oct. 15-20, 2000, Piscataway, NJ, USA IEE, US vol. 3, Oct. 2000 pp. 1758-1762.

Lee, K.J. et.al. "Use of Forward Projection to Correct Patient Motion During SPECT Imaging" Phys. Med. Biol., vol. 43, 1998, pp. 171-187.

Qi, J., et.al., Correction of Motion in PET Using Event-Based Rebinning Method: Pitfall and Solution, J. Nucl. Med., Jun. 19, 2002, p. 164P.

Qi, J., et.al., List Mode Reconstruction for PET with Motion Compensation: a Simulation Study Biomedial Imaging 2002. IEEE Int'l Symposium on Jul. 7-10, 2002 Piscataway, NJ Jul. 2002 pp. 413-416.

Thielemans, K. et.al., "Image Reconstruction of Motion Corrected Sinograms" 2003 IEEE Nuclear Science Symposium Conference Record. 2003 IEEE Nuclear Science Symposium and medical Imaging conference. Portland Or, Oct. 19-25, 2003, IEE Nuclear Science Symposium Conference Record, NY, NY vol. 5 of 5, Oct. 19, 2003, pp. 2401-2406.

PCT/GB2004/004379 Int'l Search Report Jul. 2005.

GB0324374.8 Search resort Apr. 2004.

PCT/GB2004/004379 Int'l Preliminary Report on Patentability Jan. 2006.

\* cited by examiner

METHOD OF, AND SOFTWARE FOR, CONDUCTING MOTION CORRECTION FOR A TOMOGRAPHIC SCANNER

This application is a filing under 35 U.S.C. 371 of international application number PCT/GB2004/004379, filed Oct. 14, 2004, which claims priority to application number 0324374.8 filed Oct. 17, 2003, the entire disclosure of which is hereby incorporated by reference.

FIELD OF THE INVENTION

This invention relates to a method of, and computer software for, conducting motion correction for a tomographic scanner, in particular but not exclusively a positron emission tomography (PET) scanner.

BACKGROUND OF THE INVENTION

A typical emission scan using a PET scanner begins with the injection of a solution including a tracer, which is a pharmaceutical compound including a radio-isotope with a short half-life, into the subject. The subject may be human or animal. The tracer moves to, and is typically taken up, in one or more organs in the subject according to biological and biochemical processes which occur within the subject. When the radio-isotope decays, it emits a positron, which travels a short distance before annihilating with an electron. This annihilation produces two high energy photons propagating in opposite directions. The PET scanner includes a photon detector array arranged (usually in a ring-shaped pattern) around the scanning area. If two photons are detected within a short timing window, a so-called "coincidence" is recorded along a line of response (LOR) connecting the two detectors. Coincidence counts along each LOR are listed each time a coincidence is detected between the corresponding detector pair, and subsequently the list is processed by, for each event, incrementing a data storage part referred to as a sinogram bin to build up a sinogram. The output sinogram is typically processed using image reconstruction algorithms to obtain volumetric medical images of the subject.

For quantitative results from PET images, attenuation correction generally forms one of the data correction stages. In a conventional PET scanner, the scanner is provided with one or more positron emitter rod sources, formed of a material such as $^{68}$Ge, which emit dual annihilation photons. To derive attenuation factors, two acquisitions using the rod sources are conventionally used—a blank scan, in which the subject being scanned is not present in the scanning area (typically, the scanner is empty except for the presence of the sources) and a transmission scan in which the subject is present in the scanning area. Since the source material is a positron emitter, the two photons arising from the annihilation of a positron and an electron are acquired in coincidence, in the same manner as with an emission scan. Conventionally, the results of the blank scan are then divided by the results of the transmission scan to derive an attenuation sinogram. The attenuation sinogram is then used to correct the emission scan for attenuation.

Typical PET scanners have detector arrangements which do not rotate during an acquisition. Typically, the detectors are arranged in two or more banks of detector rings. Alternatively, the detectors may be arranged in a non-ring-shaped pattern. In any case, there will generally be directions in which coincidences are not detectable due to the geometry of the detector array, since the scanner has a finite field of view and there may be "blind spots" due to gaps between the detectors, etc.

With the increasing resolution of PET scanners, subject movement becomes an important degrading factor in the quality of the data. For example with brain scans, head movement causes a time-varying rigid body transformation of the brain, and hence of the radioactivity distribution to be reconstructed. The head movement can be externally monitored, and the effects of the monitored movements can be corrected. Several methods have been proposed to correct for subject movement. They fall into 3 classes:

(a) Post-processing of the image using deconvolution. See for example the papery by M. Menke, M. S. Atkins, K. R. Buckley, "Compensation Methods for Head Motion Detected During PET Imaging", IEEE TNS vol. 43, (1996) 310.

(b) Multiple Acquisition Frame (MAF) methods, i.e. splitting the acquisition into short time frames (which may be triggered by a threshold on the amount of motion), followed by reconstruction each short time frame, realignment of the images and then combining all these images into one image. See for example the paper by Y. Pickard, C. J. Thompson, "Motion correction of PET images using multiple acquisition frames", IEEE TMI vol. 16 (1997) 137.

(c) Acquiring the data in list-mode and realigning the events according to the known motion before binning them into a sinogram, followed by reconstruction of the sinogram. See for instance the paper by P. Bloomfield, T. J. Spinks, J. Reed et al., "The design and implementation of a motion correction scheme for neurological PET", PMB 48 (2003) 959 for a discussion of the merits of these methods and more complete references, and a paper by S. K. Woo, H. Watabe, et al, "Sinogram-based motion correction of PET Images using Optical Motion Tracking and List-mode Data", Conf. Proc. IEEE MIC 2002. Both the Bloomfield et al. paper and the Woo et al. paper describe reconstructing the data with a Fourier Rebinning (FORE) algorithm followed by a Filtered Back Projection (FBP) algorithm, and mention that artefacts in the images depending on the type of motion.

A paper by H. Watabe, N. Sato, et al, "Correction of Head Movement Using Optical Motion Tracking System during PET Study with Rhesus Monkey", "Brain Imaging Using PET" eds. M. Senda, Y. Kimura, P. Herscovitch, Academic Press ISBN 0-12-636651-9 p 1-8 2002 observes that in 2D PET, rotation can move LORs to oblique LORs, and suggested a solution which essentially amounts to a Single Slice Re-Binning (SSRB) approximation.

It is an object of the present invention to provide improvements relating to motion correction for tomography, in particular but not exclusively PET scanners.

In a poster entitled "Correction of Motion in PET using Event-Based Rebinning Method: Pitfall and Solution" by Jinyi Qi and R. H. Huesman of the Centre for Functional Imaging, Lawrence Berkeley National Laboratory, a method of event-by-event motion correction is proposed in which LORs are re-aligned, and some LORs are re-scaled due to the fact that not all LORs are visible to the scanner once a patient has moved. However, some readings along LORs may be so low that resealing would lead to the introduction of significant errors, rather than reducing such errors.

In accordance with one aspect of the present invention there is provided method of conducting motion correction for a tomographic scanner including a detector array for detecting radiation to generate detector data, wherein the method comprises:

storing detector data collected during a data acquisition period, said detector data being indicative of:
  i) directions along which radiation is detected; and
  ii) quantities of radiation detected in different of said directions;

storing movement data representing movement of the subject during the data acquisition period; and motion correcting said detector data using said movement data and a motion correction algorithm to calculate motion corrected detector data, wherein said motion correcting step comprises processing said detector data by:

a) realigning directions of at least some of said detector data on the basis of said movement data; and b) altering quantities of at least some of said detector data on the basis of said movement data, such that at least some of said detector data are both realigned and altered in quantity, wherein said altering quantities step comprises calculating estimates of first detector data based on second, different, detector data.

In preferred embodiments of the invention, the altering quantities step comprises both scaling quantities upwards and calculating estimates based on other of said detector data. Preferably, the method comprises selectively either scaling a quantity upwards or replacing a quantity with a calculated estimate. Alternatively, the method may comprise altering the quantity so that the altered quantity takes into account both the original quantity and a separately calculated quantity (for example, by weighted average of a rescaled quantity and a separately calculated estimate.)

Typically, the motion corrected data will then be used as input data for an image reconstruction algorithm to produce a reconstructed image. The present invention provides a new motion correction procedure which can be used to reduce the appearance of artefacts in the reconstructed images due to particular types of motion of the subject, including translation along the scanner axis and rotation about a rotation axis orthogonal to the scanner axis.

Aspects of the invention further include computer software and a scanner system arranged to carry out the method of the invention.

Further features and advantages of the present invention will become apparent from the following description of preferred embodiments of the present invention, made by way of example only with reference to the accompanying drawings.

DETAILED DESCRIPTION OF PREFERRED EMBODIMENTS

Figure 1:
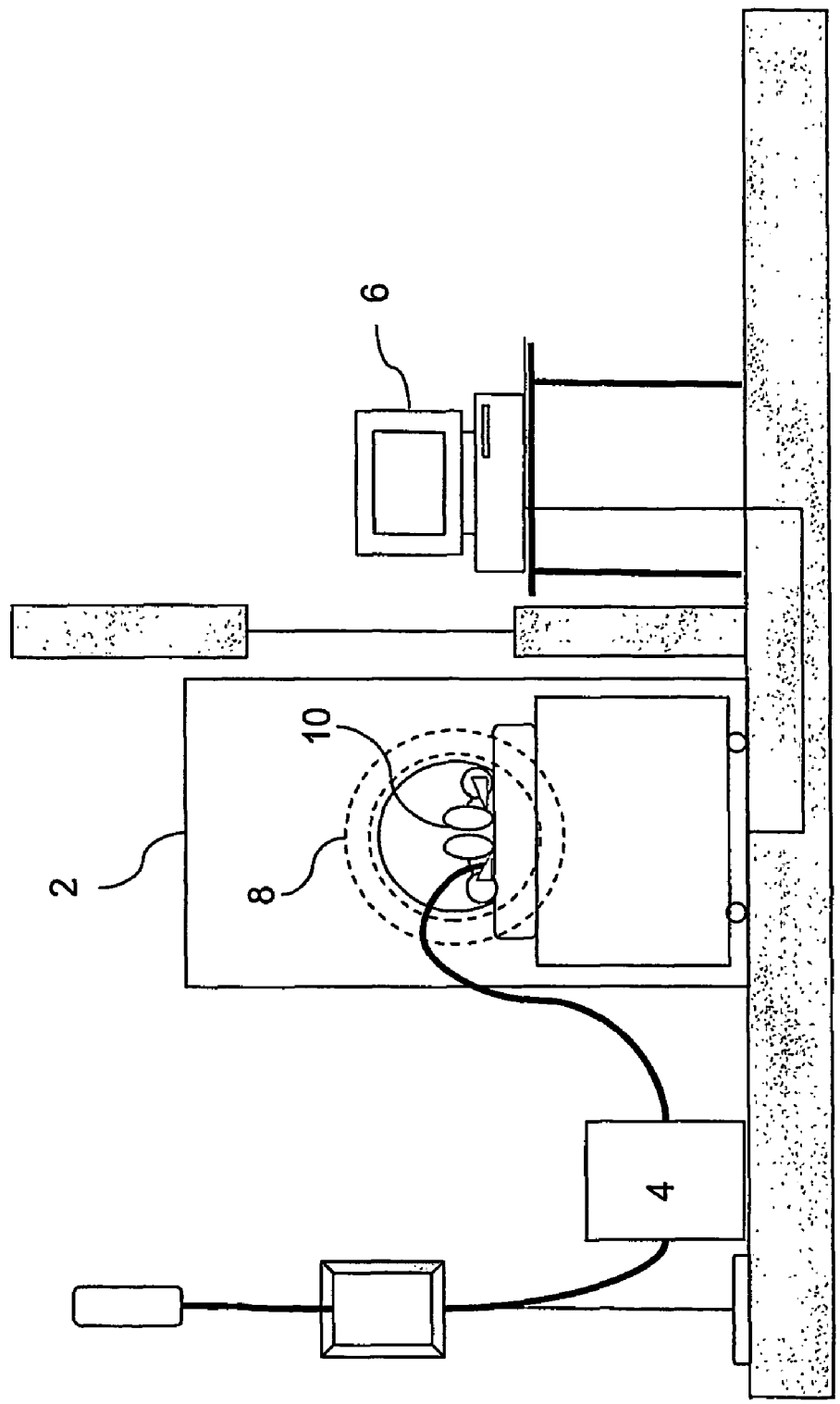
FIG. 1 is a schematic diagram of a PET scanning facility.

Referring now to FIG. 1, a PET scanning facility, arranged in accordance with an embodiment of the invention, is shown, which includes a PET scanner 2, a tracer generator module 4 and an operator computer terminal 6. The scanner 2 includes a detector array 8 arranged about a scanning area, in which a subject 10 is located during a transmission scan and during an emission scan.

One embodiment of the invention relates to a non-rotating PET scanner. For example, a PET scanner of the ECAT EXACT3D™ type is used. In this example, the detectors in the detector array 8 are arranged in square detector blocks, each containing multiple detector elements. The detectors are arranged in multiple rings of detector blocks, the rings being arranged adjacent one another along a scanner axis.

Figure 2:
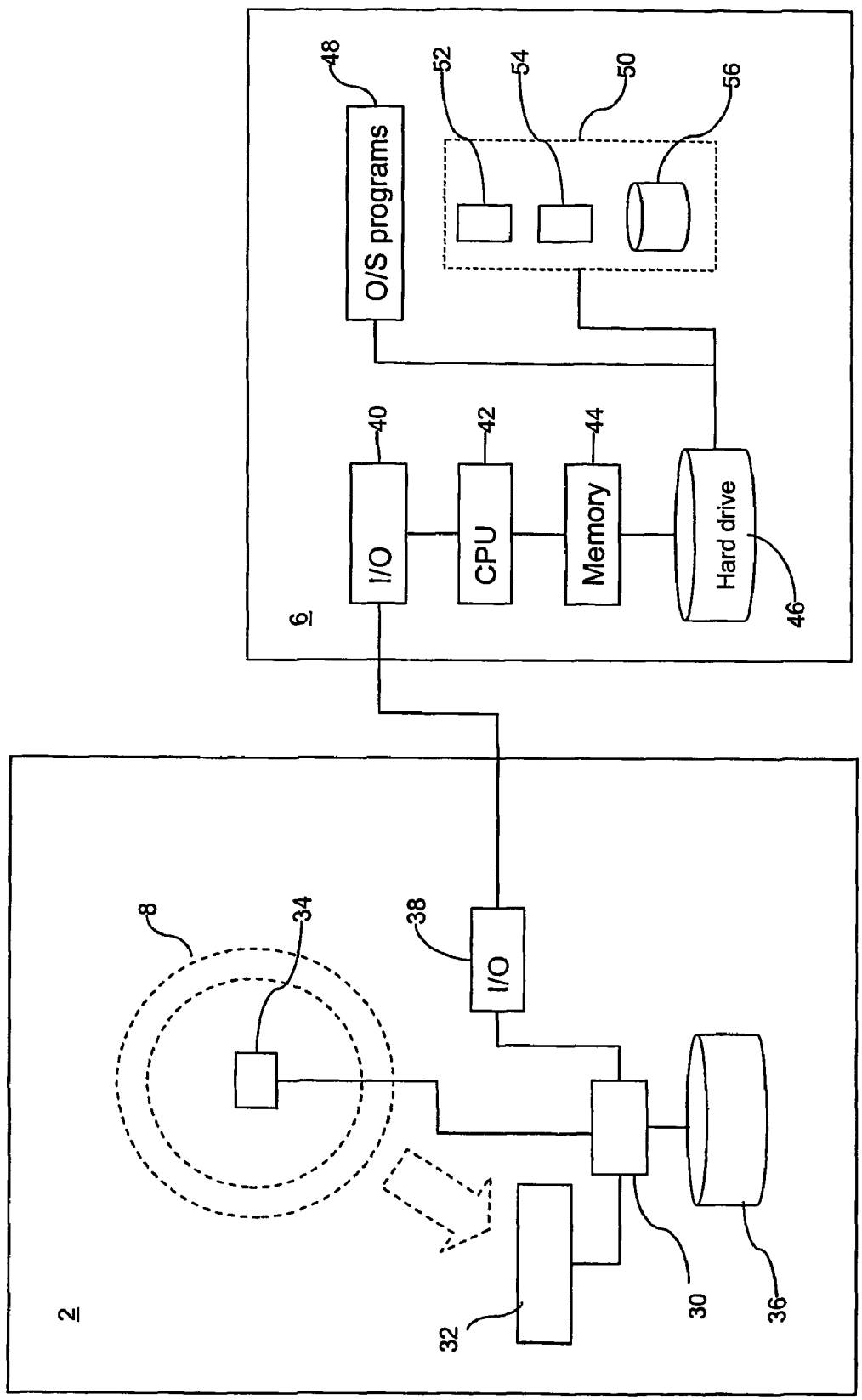
FIG. 2 is a schematic diagram of data processing components in a PET scanner and an associated data processing terminal.

As shown in FIG. 2, the PET scanner 2 includes a control unit 30, detection data processing circuitry 32, a motion detector 34, a data store 36 for storing the detector data and movement data, and an Input/Output (I/O) device 38.

In this embodiment, the motion detector 34 is in the form of a Polaris™ measurement device (produced by Northern Digital Inc. of Waterloo, Canada), which measures the motion of a plate with four reflectors using infrared radiation. This plate is attached to a neoprene cap closely fitting the head of the subject, so as to track movement of the head, to produce movement parameters indicating translational motion along three orthogonal axes and rotational motion about three orthogonal axes.

The computer terminal 6 includes a central processing unit (CPU) 42, memory 44, hard disc drive 46 and I/O device 40, which facilitates interconnection of the computer 6 with the PET scanner 2. Operating system programs 48 are stored on the hard disc drive 46, and control, in a known manner, low level operation of the computer terminal 6. Program files and data 50 are also stored on the hard disc drive 46, and control, in a known manner, outputs to an operator via associated devices. The associated devices include a display, a pointing device and keyboard (not shown), which receive input from, and output information to, the operator via further I/O devices (not shown). Included in the program files 50 stored on the hard drive 46 are a motion correction software application 52 and an image reconstruction software application 54. A database 56 is used to store the detector data and movement data transferred from the PET scanner 2.

In acquisition mode, the detection data processing circuitry 32 processes all events detected in the detector array 8, and by using a coincidence timing window, detects coincidences between the events which are recorded as real coincidence counts. These coincidence counts are then output in list-mode to data store 36, where it is stored a list-mode file for subsequent processing. In parallel with the data acquisition by the radiation detectors, position data is collected at regular, sub-second intervals (e.g. 10 Hz) from motion detector 34 and also sent to data store 36 for subsequent processing.

Figure 3:
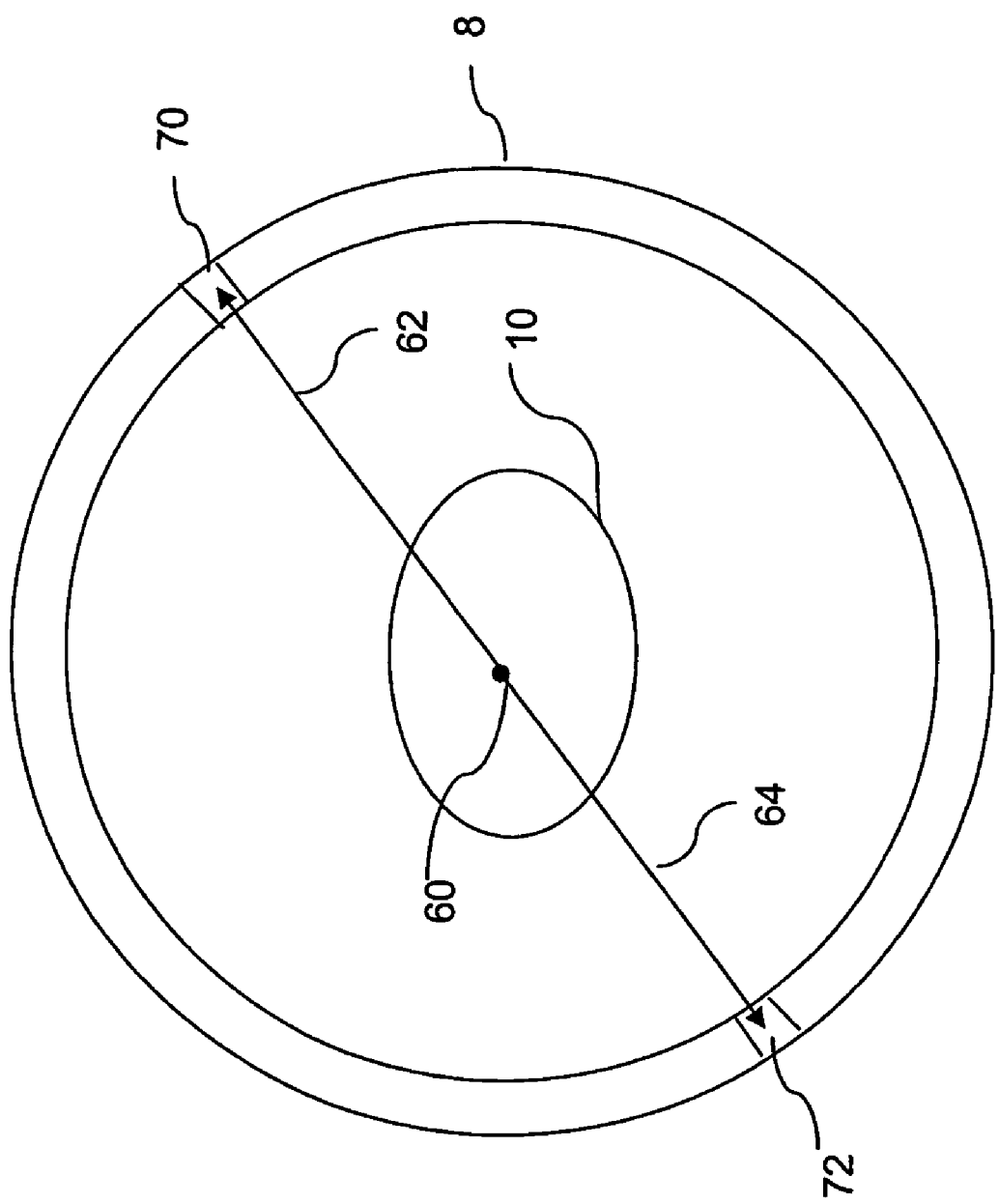
FIG. 3 is a schematic cross section of the arrangement within a PET scanner during an emission scan acquisition.

FIG. 3 illustrates features of operation of the PET scanner during an emission scan. During an emission scan, the subject 10 is placed in the scanning area and contains the tracer generated by the tracer generator module 4. FIG. 3 shows a positron emission event being registered in the detector array 8. The positron 60 annihilates and generates a first photon 62 travelling in one direction and a second photon 64 travelling in an opposite direction. The first photon is detected by a detector element 70 on one side of the detector array 8, and the second photon 64 is detected in a different detector element 72 on the other side of the detector array 8. As described above, the detection data processing circuitry 32 registers the two as a coincidence along the LOR defined between the two different detectors 70, 72.

Figure 4:
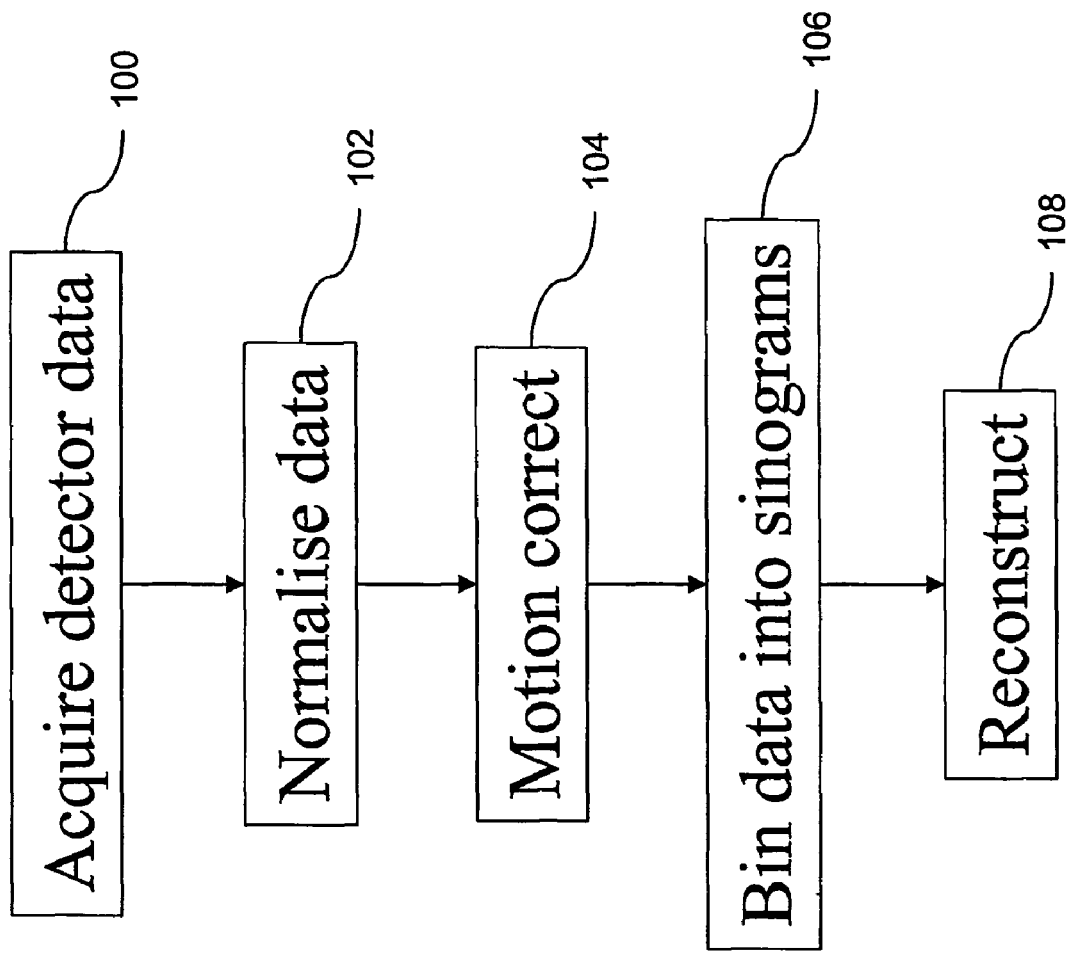
FIG. 4 is a flow diagram illustrating a general data processing procedure conducted, including motion correction according to an embodiment of the invention.

The motion correction procedure carried out using motion correction software application 52 includes, in one embodiment of the invention, the stages illustrated in FIG. 4. These are the stages of acquiring the detector data in list-mode 100, weighting each list-mode event with the normalisation factor appropriate for the original detector pair 102, performing motion correction 104, binning the realigned list-mode events into sinograms 106, and image reconstruction 108.

In the realignment during motion correction 104, for each event in the list-mode file, the LOR is repositioned according to the motion parameters derived from the motion detector 34. This can be done at sub-second time-resolution, since the list-mode data has a time resolution which is higher than that of the motion detector data (which is itself available at frequencies up to 20 Hz.) The reoriented LOR is then stored in an appropriate sinogram bin using an interpolation method such as nearest neighbour interpolation.

Since the scanner has a finite field of view the motion corrected LORs can sometimes fail to fill the whole 3D sinogram, with parts of the sinogram being completely missing or having too low values because they are 'filled' only partly during the whole acquisition.

Two particularly problematic cases have been identified: axial translation and rotation around an axis which is not parallel to the scanner axis (for instance caused by the subject nodding). These two problems are illustrated in FIGS. 5 and 6 respectively, which show schematically a uniform cylinder phantom 200 placed in the scanner, and moved between two discrete positions, from a first position 200A to a second position 200B (FIG. 5) and a third position 200C (FIG. 6).

Translation Along the Axis of the Scanner

Figure 5:
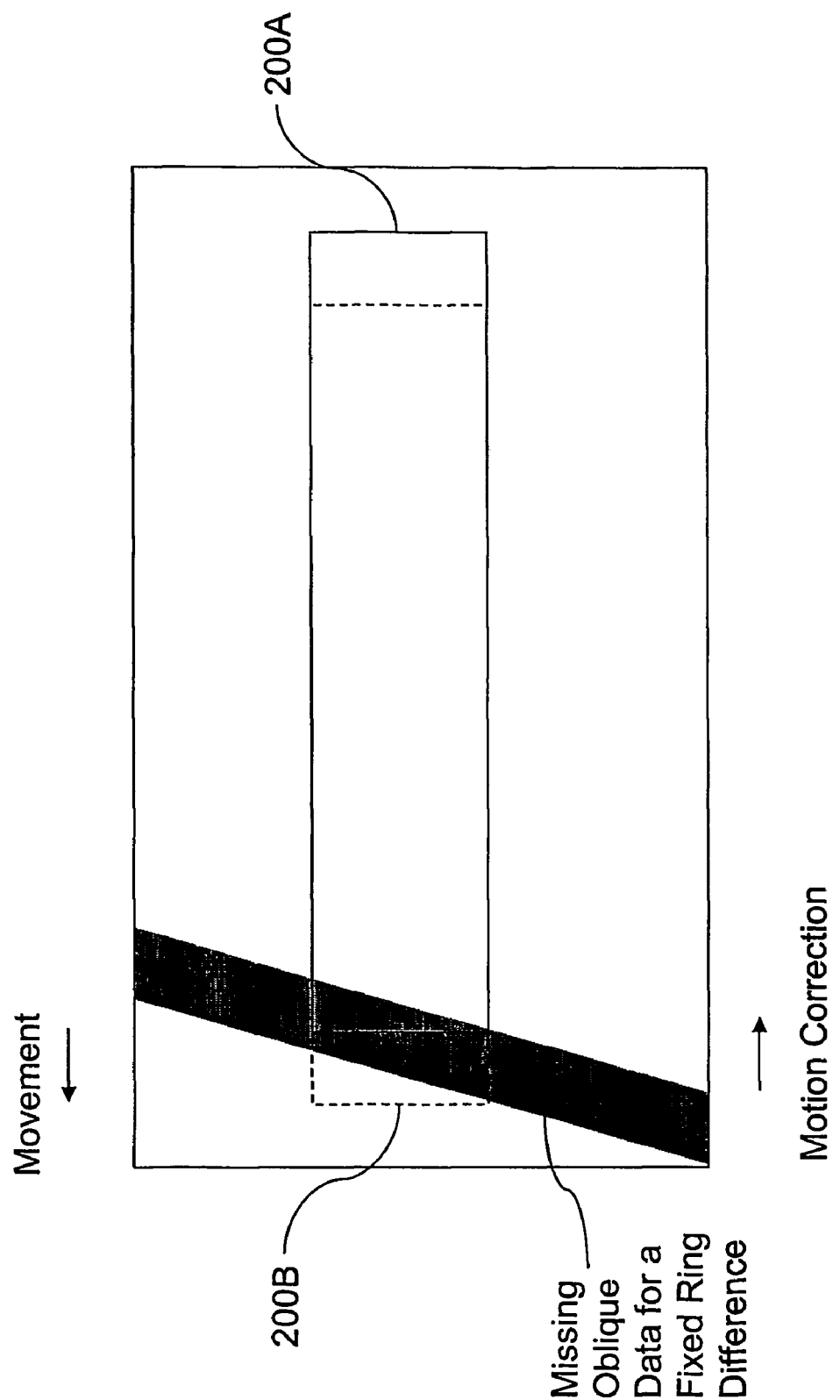
FIG. 5 is an illustration of areas of missing data in a sinogram due to axial linear motion of the subject during an emission scan acquisition.
Figure 6:
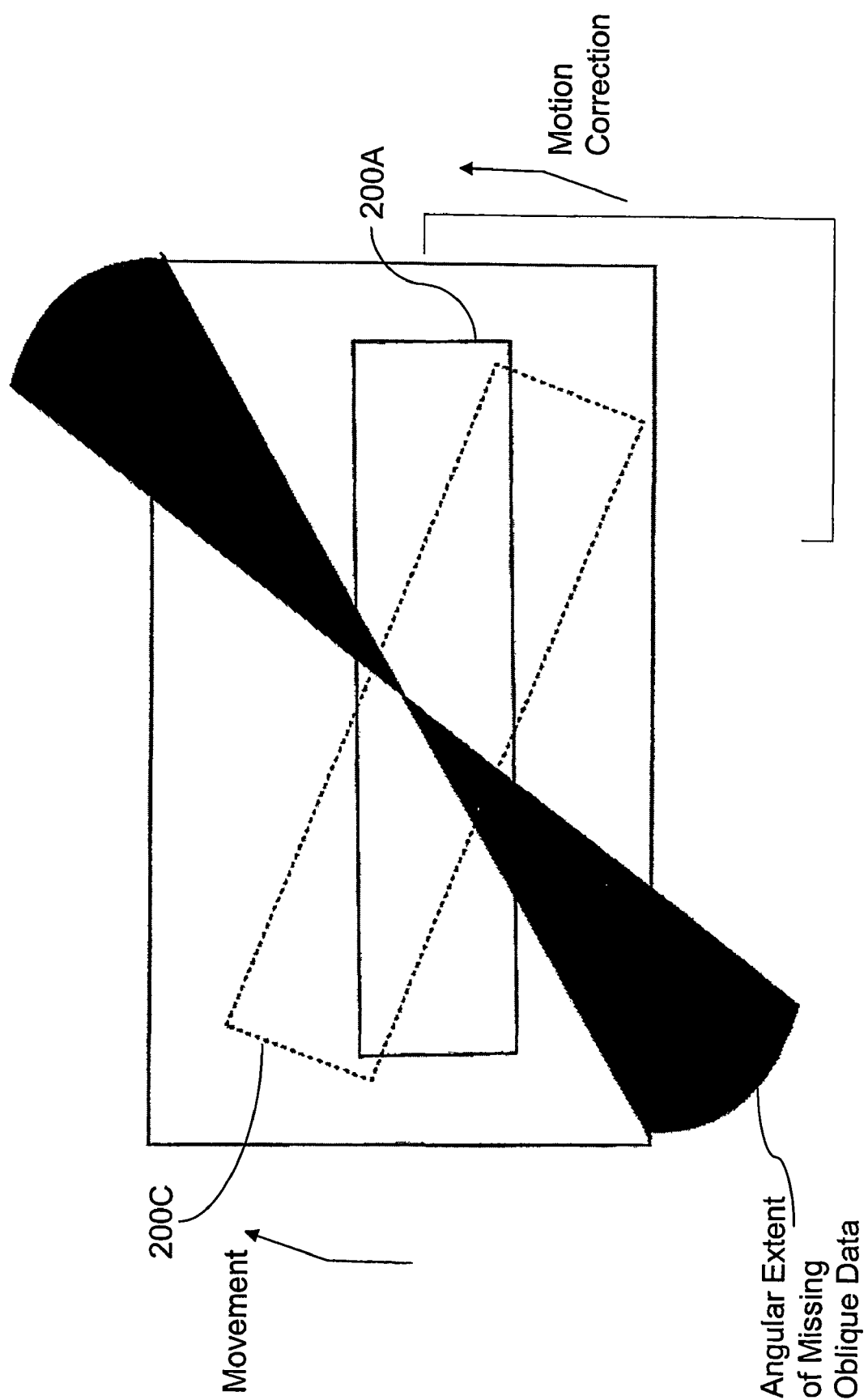
FIG. 6 is an illustration of areas of missing data in a sinogram due to non-axial rotational motion of the subject during an emission scan acquisition.

FIG. 5 illustrates the case in which the subject has moved outward (i.e. away from the bed end furthest from the scanner), and the motion correction is such as to tend to reposition it towards the centre of the scanner. There is no measured data that will be repositioned into the set of non-oblique LORs at the end of the detector array. So, the reconstructed image will have problems in the end-planes.

Further, in a 3D PET acquisition, data for oblique LORs are also acquired. Oblique LORs are those in which each end of the LOR is on a different ring (the number of rings separating the respective sides of the LOR is referred to as a ring-difference.) For each ring-difference, the same number of oblique end-LORs will be affected, as can be seen on FIG. 5, which illustrates the missing oblique data for a selected ring difference. These missing oblique end-LORs would have, had the subject not moved, measured parts throughout the subject which are not near the ends of the scanner. In fact, for the maximum ring difference, the missing LORs go right through the centre of the scanner axis. If the fact that these end-LORs are erroneous is not taken into account, the resulting image will show artefacts. The type of artefact depends on the reconstruction algorithm used, as each algorithm reacts differently to inconsistent data.

As an example, a 'sagittal' slice was taken through the reconstructed image of a motion corrected cylinder, i.e. a slice through the axis of the scanner. An analytic reconstruction algorithm called three dimensional reprojection (3DRP) was used. Artefacts were clearly visible in the object relatively far from the end-planes. This can be explained by the edge enhancement of the Colsher filter together with the fact that, in this experiment, the data for the end-LORs for a fixed ring difference were underestimated, while the reprojected data were not. The artefacts obtained using the FORE analytic reconstruction algorithm were less severe, but were still clearly visible in areas away from the edge of the cylinder.

Rotation Around an Axis Orthogonal to the Scanner Axis

FIG. 6 illustrates the case with rotation of the subject about an axis orthogonal to the scanner axis. On realignment during the motion correction procedure, the set of oblique LORs, those making angles relative to the line connecting diametrically opposite detectors in the plane of the moment within the angular extent of the rotational movement, will have missing data. Therefore, if the rotation is too large (i.e. larger than the axial acceptance angle of the scanner), the motion corrected segment will again cause problems in the throughout the scanner, not only in the end-planes.

Continuous Motion

In this case, the sinogram resulting after the binning process can be seen to be simply a superposition of sinograms obtained for very small time duration. Some bins in the projection data produced by the rebinning procedure described above will have the same value as if no motion had occurred, but others will have a smaller value, depending on how many of these very short time frames would fill data in the bin.

In the notation used herein, elements of the (3D) sinogram are indexed by b (for bin). The projection data that is obtained for the subject in the position at time t will be denoted by $s^t_b$ and the reference position, at which the reference sinogram is taken, is denoted with a subscript r. The number of very short time frames is denoted by N. The motion correction procedure of binning each list-mode event into a sinogram bin can be seen as a linear process which can be conceptually encoded in a matrix $M^t$ that will change with t:

$$s = \frac{1}{N} \sum_t M^t s^t \qquad (1)$$

Note that this matrix $M^t$ combines the repositioning of the LORs with the binning into a sinogram. So, it would have dimensions n×m where n is the number of sinogram elements after binning, and m is the number of possible LORs, with n<m being the usual case.

Each motion corrected sinogram should be the same as the reference sinogram, except for the missing data, at least if discretisation and interpolation errors are ignored. So:

$$M^t s^t \approx \mathrm{diag}(d^t) s^r \qquad (2)$$

where $\mathrm{diag}(d^t)$ is a diagonal matrix with elements $d^t_b$ on the diagonal which are 0 where the data are missing, 1 for bins which were completely in the field of view, and potentially between 0 and 1 for bins at the border between these two regions. So, the motion corrected sinogram will have elements which are scaled versions of the reference sinogram:

$$s_b = d_b s^r_b, \qquad (3)$$

with:

$$d_b = \frac{1}{N} \sum_t d^t_b \qquad (4)$$

Since these scale factors are not all equal to each other, the motion corrected sinogram will be inconsistent (i.e. does not correspond to the sinogram of the subject in its reference position) and the reconstruction process will have to be adapted to take this into account. Otherwise, artefacts will occur.

Making the Motion Corrected Sinogram Consistent

When a scale factor $d_b$ is non-zero, we could just divide the detector data $s_b$ by it. However, for small scale factors division would lead to noise enhancement in the data. Therefore, a threshold is used so that when the scale factor is smaller than a threshold, the corresponding bin cannot be corrected by rescaling. Instead, an estimate of the value which should be in the bin is separately calculated. From an initial estimate of the image, taken from only the non-oblique LORs, referred to as the direct sinograms. This is then forward projected to obtain an estimate of the value $s^r_b$ of the bin in the reference sinogram.

A consistent sinogram can be estimated as:

$$s^c_b = \begin{cases} s_b/d_b & \text{if } d_b > a_b \\ s^f_b & \text{otherwise} \end{cases} \quad (5)$$

where $s^f_b$ is the value of the forward projection of the initial image, and $a_b$ is the threshold. The threshold can be a global threshold applied to all bins, or may be a local threshold varying depending on the bin identity.

The motion correction software application 52 preferably includes functionality allowing the threshold, whether global or local, to be varied between different acquisitions, depending on the quality of the data obtained.

Construction of the Initial Estimate of the Image

As mentioned above, the initial estimated image can be produced by a reconstruction of the direct sinograms. However, even the direct sinograms can have missing data, especially in the end planes. One solution for this is to discard those end planes of the initial image that are too corrupted. In the case that too many direct sinograms are corrupted by rotation, an alternative would be to reconstruct the initial image from a set of oblique projections orthogonal to a direction not parallel to the scanner axis.

With both these procedures, it is possible to end up with an initial image that is shorter than the scanner field of view. It is then important to consider which LORs are used in the final reconstruction process. The values of the estimated bins $s^f_b$ will correspond to an object which is as long as the initial image, while the motion corrected data $s_b$ could have contributions of activity which does not overlap with the initial image. These bins are discarded, as otherwise the data would still have potential inconsistencies.

The end result of this procedure will be a final reconstructed image that will have fewer planes than usual (i.e. the same number as in the initial image), but the image will have no artefacts.

Determination of the Scale Factors

The scale factors $d^t_b$ defined in equation (2) are (approximately) independent of the sinogram that is being motion corrected. Their role is similar to the (inverse of the) usual normalisation factors in PET.

The scale factors can be computed by motion correcting a data set which has 1 in every LOR, and a set of LORs is sampled after the motion correction to produce scale factors which vary across the entire sinogram.

Both sinograms in equation (2) have now all elements equal to 1, so:

$$d^t = M^t u_m \quad (6)$$

with $u_m$ a 1×m column vector with all elements equal to 1. This can be computed by a loop over all possible LORs, repositioning the LOR, and storing 'events' in the sinogram using the same interpolation as used in the actual motion correction.

Computing the scale factors $d_b$, which are averaged over the whole frame using equation (4), is highly processor-intensive. Several optimisations are possible. The number of time steps in the sum can be made smaller as the motion parameters tend to vary smoothly aside from sudden jumps. In addition, if an appropriate interpolation scheme is used during the motion correction, the set of bins which has scale factor 1 is a geometrically connected region. This means that the scale factors $d_b$ can first be computed in with low precision, and that then edges in the resulting sinogram can be recomputed with higher precision.

Determination of the Thresholds

The role of the thresholds $a_b$ is to avoid noise amplification. A number of approaches are possible. For instance, strong smoothing on the motion corrected sinogram s can be applied to obtain a rough estimate of the noise level in each bin which would allow lower threshold values to be selected for the higher values in each bin.

This means the thresholds can be chosen to have lower values where the motion corrected data is less noisy. Because of the Poisson nature of PET data, the relative noise level decreases with higher values of the mean (over repeated experiments) value of $s_b$. However, the data in a single sinogram bin is generally too noisy to use as an estimate for this mean value. This can be remedied by applying a strong smoothing on the motion corrected sinogram s to obtain a rough estimate of the noise level in each bin. The threshold can then be made lower for higher values of the bin in the smoothed sinogram. After this, the smoothed sinogram is discarded. Alternatively, a global threshold (i.e. independent on b), may be used. The global threshold may be varied in dependence on a factor such as the total number of counts in a sinogram.

The higher the threshold, the more data will be replaced by the separately calculated forward projections. Since the estimated forward projections generally have lower resolution compared to the measured data, setting the threshold higher will result in images with lower resolution but less noise.

Normalisation for Detection Efficiencies

In practice, different LORs will have different detection efficiencies, which can be used to form a detection efficiency sinogram $\epsilon$. The detected sinogram should be normalised to correct for these efficiencies. In one embodiment this is done before binning (i.e. the detection efficiency factor is obtained for an event, the LOR is repositioned, the event is weighted with the inverse of the detection efficiency factor and interpolated into the motion correct sinogram).

An alternative solution is to not perform normalisation during binning, but to include these scanner normalisation factors in the scale factors referred to above. In the case without motion correction, this has been shown to give better noise properties. To do this, the motion correction sinogram is obtained as in equation (1), where now $s^t$ is however not precorrected for detection efficiencies. The result will again be (almost) proportional to a reference sinogram as in equation (3). Take as reference what would have been obtained without motion, but in this case with normalisation for detection efficiencies. These scale factors can then be found by looking at smooth objects. That is, by assuming that the reference data is a sinogram filled with 1s. The non-normalised measured data will then be the detection efficiency sinogram $\epsilon$. The analogue of equations (4) and (6) is now:

$$d = \frac{1}{N}\sum_t M^t \varepsilon \quad (7)$$

These scale factors will no longer all be less than or equal to 1, as they depend on $\varepsilon$. This can be taken into account when setting the thresholds.

Other Precorrections

If the list-mode data contains delayed events, then randoms correction can be performed during the binning by subtracting the delayed events after repositioning. If some other way of estimating the randoms is used, the motion would have to be taken into account.

For scatter, it can be assumed that all of the scatter is due to the subject. In that case, the scatter distribution is just moved along with the subject resulting in a scatter distribution which is exactly the same as the scatter distribution of the subject in the reference position. So, any existing scatter correction procedure can be used on the motion corrected data. However, some scatter is due to non-moving objects, such as the bed and the scanner itself. This can be corrected by estimating the scatter distribution caused by the non-moving objects in multiple positions and motion correcting the results.

Finally, there is attenuation correction. However, after motion correction, the attenuation factors are the same as those for the subject in the reference position. Preferably, the reference position is chosen to be the position of the subject during transmission scanning.

Description of Exemplary Specific Procedure

A step-by-step description of one embodiment of the motion correcting procedure follows:

1. Obtain attenuation coefficients of subject in the reference position. This can be done using the following procedure:
   (i) Perform a blank and transmission scan.
   (ii) Reconstruct an image representing the attenuation map of the subject using the transmission and blank data.
   (iii) Move the attenuation map to the reference position by reinterpolation.
   (iv) Forward project this attenuation map and exponentiate.
2. Perform a list-mode emission scan while tracking the motion of the subject.
3. Bin the list-mode data into a motion corrected sinogram by repositioning the LORs. Normalise the events for detection efficiencies.
4. Obtain the scale factors equation (4) or (7) depending on whether events were normalised or not in the previous step.
5. Obtain thresholds $a_b$.
6. Divide the motion corrected sinogram by the scale factors $d_b$, unless the scale factor is too small. In that case, rescale the data with the threshold:

$$s_b^m = \begin{cases} s_b/d_b & \text{if } d_b > a_b \\ s_b/a_b & \text{otherwise} \end{cases}$$

7. Correct the resulting sinogram $s^m$ for scatter and attenuation as usual. Call the result $s^P$.
8. Reconstruct initial image from a consistent subset of this precorrected sinogram. This image can be shorter than the field of view.
9. Reduce the size of the 3D sinogram $s^P$ such that only LORs are considered which intersect the initial image, but no other parts of the subject.
10. Merge the forward projections (by using line integrals) of the initial image into the precorrected sinogram:

$$s_b^c = \begin{cases} s_b^P & \text{if } d_b > a_b \\ s_b^f & \text{otherwise,} \end{cases}$$

where $s^f$ is the forward projected data.

The result of this procedure is a consistent, fully-precorrected 3D sinogram (ignoring the effects of noise). This can then be passed to any known 3D reconstruction algorithm that works on fully precorrected data.

Alternatives to the above-described embodiments are envisaged. Whilst in the above embodiment, the detector data is output to a list-mode file which is then processed offline to perform motion correction, in an alternative embodiment of the invention the motion correction system of the present invention may be built into a scanner, so as to provide online motion correction of LORs which can then be used to directly generate a sinogram.

In the above-described embodiments, where the original measured data is inconsistent due to motion of the subject, the original measured data can be either rescaled or replaced with a separately calculated value. Alternatively, a weighted average of the two types of corrected data may be taken when the scale factor falls below the preset threshold; or a varying weighting can be applied in dependence on the scale factor value.

It should be noted that the invention applies also to PET scanners in general, both non-rotating and rotating. Further, although the above-described embodiment relates to a PET system, the method of the invention could also be used in other systems of tomography, such as x-ray computer tomography (CT) and single photon emission computer tomography (SPECT).

The motion correction method of the invention may be used in combination with analytic image reconstruction algorithms such as 3DRP, FAVOR, BPF, etc. Alternatively, or in addition, the method of the invention may be used with analytic rebinning algorithm such as FORE, FORE-X, FORE-J, in combination with an iterative reconstruction algorithm, or indeed iterative algorithms which work on precorrected data.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of conducting motion correction for a tomographic scanner including a detector array for detecting radiation to generate detector data, wherein the method comprises:
   storing detector data collected during a data acquisition period in one of a data store of the scanner and a memory of a computer connected to the scanner, said detector data being indicative of:

i) directions along which radiation is detected; and
ii) quantities of radiation detected in different of said directions;
storing movement data representing movement of the subject during the data acquisition period in one of a data store of the scanner and a memory of a computer connected to the scanner; and
motion correcting said detector data using said movement data and a motion correction algorithm to calculate motion corrected detector data, said motion correcting step being performed by a computer connected to the scanner;
wherein said motion correcting step comprises processing said detector data by:
a) realigning directions of at least some of said detector data on the basis of said movement data; and
b) altering quantities of at least some of said detector data on the basis of said movement data,
such that at least some of said detector data are both realigned and altered in quantity,
wherein said altering quantities step comprises calculating estimates of first detector data based on second, different, detector data,
characterised in that said altering quantities step comprises either:
selecting whether to scale an original detected quantity of said first detector data upwards or to replace the original detected quantity of said first detector data with a said calculated estimate; or
altering the original detected quantity of said first detector data so that the altered quantity takes into account both the original detected quantity and a said calculated estimate.

2. A method according to claim 1, wherein said estimates are calculated using forward projection from said second detector data.

3. A method according to claim 1, wherein if the method comprises altering the original detected quantity quantity so that the altered quantity takes into account both the original detected quantity and a said calculated estimate, the method comprises selecting a weighting between the original detected quantity and the calculated estimate to generate said altered quantity.

4. A method according to claim 3, wherein said selecting whether to scale or replace is performed on the basis of a threshold.

5. A method according to claim 4, wherein said threshold is variable.

6. A method according to claim 4, wherein a value indicating an amount of scaling deemed appropriate for a quantity is determined, and the value is compared to the threshold in order to determine whether to scale the quantity upwards or to replace it with a calculated estimate.

7. A method according to claim 1, further comprising performing image reconstruction using said motion corrected detector data.

8. A method according to claim 7, comprising performing image reconstruction using one of an analytic image reconstruction algorithm and an analytic rebinning algorithm.

9. A method according to claim 8, wherein said algorithm is one of 3DRP, FAVOR, BPF, FORE, FORE-X and FORE-J.

10. A method according to claim 1, wherein said scanner is a positron emission tomography (PET) scanner.

11. A method according to claim 10, wherein said detector data is 3D PET detector data.

12. Computer software stored on a computer storage medium for conducting motion correction for a tomographic scanner including a detector array for detecting radiation to generate detector data, wherein the software is configured to:
store detector data collected during a data acquisition period, said detector data being indicative of:
i) directions along which radiation is detected; and
ii) quantities of radiation detected in different of said directions;
store movement data representing movement of the subject during the data acquisition period; and
motion correct said detector data using said movement data and a motion correction algorithm to calculate motion corrected detector data,
wherein said motion correcting step comprises processing said detector data by
a) realigning directions of at least some of said detector data on the basis of said movement data; and b) altering quantities of at least some of said detector data on the basis of said movement data,
such that at least some of said detector data are both realigned and altered in quantity,
wherein said altering quantities step comprises calculating estimates of first detector data based on second, different, detector data:
characterized in that said altering quantities step comprises either: selecting whether to scale an original detected quantity of said first detector data upwards or to replace the original detected quantity of said first detector data with a said calculated estimate; or
altering the original detected quantity of said first detector data so that the altered quantity takes into account both the original detected quantity and a said calculated estimate.

13. A tomographic scanner system including a detector array for detecting radiation to generate detector data, wherein the scanner system is configured to:
store detector data collected during a data acquisition period, said detector data being indicative of:
i) directions along which radiation is detected; and
ii) quantities of radiation detected in different of said directions;
store movement data representing movement of the subject during the data acquisition period; and
motion correct said detector data using said movement data and a motion collection algorithm to calculate motion corrected detector data,
wherein said motion correcting step comprises processing said detector data by:
a) realigning directions of at least some of said detector data on the basis of said movement data; and
b) altering quantities of at least some of said detector data on the basis of said movement data,
such that at least some of said detector data are both realigned and altered in quantity,
wherein said altering quantities step comprises calculating estimates of first detector data based on second, different, detector data,
characterised in that said altering quantities step comprises either:
selecting whether to scale an original detected quantity of said first detector data upwards or to replace the original detected quantity of said first detector data with a said calculated estimate; or
altering the original detected quantity of said first detector data so that the altered quantity takes into account both the original detected quantity and a said calculated estimate.

* * * * *